United States Patent
De Boer et al.

(10) Patent No.: US 11,071,720 B2
(45) Date of Patent: Jul. 27, 2021

(54) CANCER THERAPY

(71) Applicant: UCL Business Ltd, London (GB)

(72) Inventors: Jasper De Boer, London (GB); Sandra Cantilena, London (GB)

(73) Assignee: UCL BUSINESS LTD, London (GB)

(*) Notice: Subject to any disclaimer, the term of this patent is extended or adjusted under 35 U.S.C. 154(b) by 0 days.

(21) Appl. No.: 16/344,757

(22) PCT Filed: Nov. 2, 2017

(86) PCT No.: PCT/GB2017/053307
§ 371 (c)(1),
(2) Date: Apr. 24, 2019

(87) PCT Pub. No.: WO2018/083481
PCT Pub. Date: May 11, 2018

(65) Prior Publication Data
US 2019/0274976 A1    Sep. 12, 2019

(30) Foreign Application Priority Data

Nov. 3, 2016 (GB) ..................................... 1618551

(51) Int. Cl.
| | |
|---|---|
| *A61K 31/145* | (2006.01) |
| *A61K 31/12* | (2006.01) |
| *A61K 31/7135* | (2006.01) |
| *A61K 33/34* | (2006.01) |
| *A61P 35/02* | (2006.01) |

(52) U.S. Cl.
CPC ............ *A61K 31/145* (2013.01); *A61K 31/12* (2013.01); *A61K 31/7135* (2013.01); *A61K 33/34* (2013.01); *A61P 35/02* (2018.01)

(58) Field of Classification Search
CPC .. A61K 31/145; A61K 31/12; A61K 31/7135; A61K 33/34; A61P 35/02
See application file for complete search history.

(56) References Cited

U.S. PATENT DOCUMENTS

| | | | | |
|---|---|---|---|---|
| 5,140,032 | A | * 8/1992 | Radecki | ................. A61K 31/55 514/221 |
| 7,816,403 | B2 | 10/2010 | Kennedy | |
| 2004/0019102 | A1 | 1/2004 | Kennedy | |
| 2006/0264384 | A1 | * 11/2006 | Johansen | ............... A61K 31/44 514/27 |
| 2010/0261712 | A1 | 10/2010 | Chedid | |

FOREIGN PATENT DOCUMENTS

| | | |
|---|---|---|
| WO | 03/008552 A2 | 1/2003 |
| WO | 2006/122007 A1 | 11/2006 |
| WO | 2011/097218 A1 | 8/2011 |
| WO | 2012/076897 A1 | 6/2012 |
| WO | 2014/128235 A1 | 8/2014 |
| WO | 2016/059247 A1 | 4/2016 |

OTHER PUBLICATIONS

Slany RK. The molecular biology of mixed lineage leukemia. Haematologica 2009;94:984-993 (Year: 2009).*
Baer et al., "Acute myeloid leukemia with 11q23 translocations: myelomonocytic immunophenotype by multiparameter flow cytomertry," Leukemia (1998) 12, 317-325.*
Rubnitzetal., "Acute mixed lineage leukemia in children: the experience of St Jude Children's Research Hospital," Blood, May 21, 2009, vol. 113, No. 21.*
Conticello et al., "Disulfiram, an old drug with new potential therapeutic uses for human hematological malignancies," Int. J. Cancer: 131,2197-2203 (2012).*
Search Report issued by UK IPO on priority application (GB 1618551.4) drawn up on Aug. 16, 2017.
International Search Report from PCT application (PCT/GB2017/053307) dated Feb. 6, 2018.
Aleem et al., "*Repurposing disulfiram for treatment of relapsed/refractory acute myeloid leukemia*", Cancer Research, 2014, abstract 3982 (http://cancerres.aacrjournals.org/content/74/19Supplement/3982).
Cantilena et al. "*Drug induced MLL fusion degradation via Hsp90 Inhibition*" (abstract), Blood, vol. 126, No. 23, 2015.
Chen et al. "*Activation of Oxidative Stress and Down-Regulation of Nuclear Factor Erythroid 2-Related Factor May Be Responsible for Disulfiram/Copper Complex Induced Apoptosis in Lymphoid Malignancy Cell Lines*", Blood, vol. 120, No. 21, 4869, Jan. 1, 2012.
De Boer et al. "*Interaction with the DNA binding domain of MLL and small molecular drug induces proteolysis of MLL-fusion proteins and ablates leukemic stem cell activity*" Blood, vol. 128, No. 22, p. 1549.
Deng et al. "*Effective elimination of adult B-lineage acute lymphoblastic leukemia by disulfiram/copper complex in vitro and in vivo in patient-derived xenograft models*" Oncotarget, vol. 7, No. 50, 82200-82212, May 17, 2016.
Gough et al. "*NUP98—PHF23 Is a Chromatin-Modifying Oncoprotein That Causes a Wide Array of Leukemias Sensitive to Inhibition of PHD Histone Reader Function*", Cancer Discovery 2014, 564-577.
Kanno et al. "*Diethyldithiocarbamate-induced cytotoxicity and apoptosis in leukemia cell lines*" Biological & Pharmaceutical Bulletin, vol. 26, No. 7, 2003, pp. 964-968.
Liu et al. "*Clinically used antirheumatic agent auranofin is a proteasomal deubiquitinase inhibitor and inhibits tumor growth*", Oncotarget, vol. 5, No. 14, 5453-5471, Jul. 30, 2014.
Lovborg et al., "*Inhibition of proteasome activity, nuclear factor-KB translocation and cell survival by the antialcoholism drug disulfiram*", Int. J. Cancer: 118, 1577-1580 (2006).
Malaguarnera et al., "*Cell death in human acute myelogenous leukemic cells induced by pyrrolidinedithiocarbamate*", Apoptosis, vol. 8, No. 5, 2003, pp. 539-545.

(Continued)

*Primary Examiner* — Jared Barsky
(74) *Attorney, Agent, or Firm* — Kilpatrick Townsend & Stockton LLP (57) ABSTRACT

The present invention relates to the treatment of mixed lineage leukemia. In particular, the present invention relates to therapies involving the induction of proteolysis of the MLL fusion proteins that result from the chromosomal translocations affecting the MLL gene at 11q23.

9 Claims, 8 Drawing Sheets

(56) References Cited

OTHER PUBLICATIONS

Papaioannou et al., "*Disulfiram/copper causes redox-related proteotoxicity and concomitant heat shock response in ovarian cancer cells that is augmented by auranofin-mediated thioredoxin inhibition*", Oncoscience, vol. 1, 21-29, Jan. 1, 2014.
Pimentel-Guttierrez et al. "*Curcumin potentiates the effect of chemotherapy against acute lymphoblastic leukemia cells via downregulation of NF-[kappa]B*" Oncology Letters, vol. 12, No. 5, 4117-4124, Sep. 30, 2016.
Rao et al., "*Hijacked in cancer: the KMT2 (MLL) family of methyltransferases*", Nature Reviews Cancer 2015, 15, 334-346.
Schmalbach et al. "*Transcriptional regulation of cytokine expression by diethyldithiocarbamate in human HL-60 promyelocytic leukemia cells*", Biochemical Pharmacology, vol. 44, No. 2, 365-371, Jul. 22, 1992.
Slany "*The molecular biology of mixed lineage leukemia*", Haematologica, The Hematology Journal: Official Organ of the European Hematology Association, vol. 94, No. 7, 984-993, Jun. 16, 2009.
Examination Report issued by the EPO dated Jan. 14, 2021 in corresponding European application No. 17795027.6, 5 pages.
Muntean, Andrew G. et al., "The Pathogenesis of Mixed-Lineage Leukemia," Annual Review of Pathology: Mechanisms of Disease, vol. 7, No. 1, Feb. 28, 2012 (Feb. 28, 2012), pp. 283-301.

* cited by examiner

CANCER THERAPY

CROSS-REFERENCE TO RELATED APPLICATIONS

This application is a national stage application under 35 U.S.C. § 371 of International Patent Application No. PCT/GB2017/053307, filed Nov. 2, 2017, which claims priority to GB Application No. 1618551.4, filed Nov. 3, 2016, the disclosures both of which are hereby incorporated by reference for all purposes in their entireties.

FIELD OF THE INVENTION

The present invention relates to the treatment of mixed lineage leukemia.

BACKGROUND TO THE INVENTION

There are two overarching types of acute leukemia, acute lymphoblastic leukemia (ALL) and acute lymphoblastic myeloid leukemia (AML), which are based on different cell lineages.

Mixed lineage leukemia is an aggressive blood cancer that occurs in pediatric and adult patients. It is characterized by the presence of MLL fusion proteins that are the result of chromosomal translocations affecting the MLL gene at 11q23.

The MLL chromosomal rearrangements juxtapose the N-terminus of MLL with a variety of different fusion partners that destroy the normal histone methyltransferase function of MLL and replace it with functions contributed by the fusion partner. The resultant fusions activate a hematopoietic stem cell-like transcriptional pathway and drive the cancer phenotype.

MLL fusion proteins can occur in both the AML and ALL leukemia types. Mixed lineage leukemia expresses surface markers of both lymphoid and myeloid lineage. The "mixed" nature or pluripotency of this cancer means it is strikingly difficult to treat and associated with particularly poor clinical outcomes. WHO have classified leukemias with 11q23 translocations as a discrete group, with an estimated 4-year event-free survival of just 24% to 55%. There are currently no approved therapies specifically indicated for this condition.

In light of the foregoing, it would be desirable to find new, more effective treatments specifically for mixed lineage leukemia. Particularly desirable would be therapies that avoid or at least mitigate the debilitating side effects associated with many current cancer therapies.

SUMMARY OF THE INVENTION

It has now been found that mixed lineage leukemia is susceptible to treatment by inducing proteolysis of the MLL fusion proteins that result from the chromosomal translocations affecting the MLL gene at 11q23.

In particular, it has surprisingly been found that thiuram disulfides and dithiocarbamic acids, such as disulfiram and its metabolite diethyldithiocarbamic acid, can induce proteolysis of MLL fusion proteins. This is associated with a block in cancer stem cell renewal. Furthermore, the killing has been found to be specific, with normal, non-cancerous cells being spared. Still further, preliminary data indicate that the levels of drug required to achieve a therapeutically effective result may be relatively low, indicating that the new targeted treatment may be associated with no, or at most only modest, deleterious side effects.

Additionally, it has been found that synergistic results can be achieved by implementing a combination therapy in which a thioredoxin reductase inhibitor and/or copper is additionally administered.

Accordingly, the present invention provides a compound for use in the treatment of mixed lineage leukemia, wherein said compound is capable of promoting the proteolyis of MLL fusion proteins associated with mixed lineage leukemia.

The present invention also provides a pharmaceutical composition that comprises: (a) a compound that is capable of promoting the proteolyis of MLL fusion proteins associated with mixed lineage leukemia; and (b) a thioredoxin reductase inhibitor.

The present invention further provides a compound that is capable of promoting the proteolyis of MLL fusion proteins associated with mixed lineage leukemia, for use in treating mixed lineage leukemia, by co-administration with a thioredoxin reductase inhibitor and optionally by co-administration with copper.

Still further, the present invention provides a thioredoxin reductase inhibitor for use in treating mixed lineage leukemia, by co-administration with a compound that is capable of promoting the proteolyis of MLL fusion proteins associated with mixed lineage leukemia and optionally by co-administration with copper.

The present invention also provides a product comprising: (a) a compound that is capable of promoting the proteolyis of MLL fusion proteins associated with mixed lineage leukemia; (b) a thioredoxin reductase inhibitor; and optionally (c) copper; as a combined preparation for simultaneous, concurrent, separate or sequential use in the treatment of with mixed lineage leukemia.

The present invention further provides use of a compound that is capable of promoting the proteolyis of MLL fusion proteins associated with mixed lineage leukemia, in the manufacture of a medicament for the treatment of mixed lineage leukemia.

Additionally, the present invention provides a method for treating mixed lineage leukemia in a patient in need thereof, the method comprising administering to said patient a compound that is capable of promoting the proteolyis of MLL fusion proteins associated with mixed lineage leukemia.

In these various aspects of the invention, the compound capable of promoting the proteolyis of MLL fusion proteins associated with mixed lineage leukemia is most typically a thiuram disulfide or a dithiocarbamic acid, or a pharmaceutically acceptable salt or ester thereof.

BRIEF DESCRIPTION OF THE FIGURES

FIGS. 2A and 2B show, as explained in Example 1.

FIG. 3 shows, as explained in Example 2, Western blot analysis after 16 hrs of diethyldithiocarbamate ("DDC")

treatment in the presence of copper of MLL-AF6 positive cell line SHI-I and MLL-AF9 positive cell line THP-1, showing proteolysis of the MLL-fusion protein.

FIGS. 4A and 4B show, as explained in Example 1.

FIGS. 6A and 6B show, as explained in Example 1.

DETAILED DESCRIPTION OF THE INVENTION

The present invention relates to the treatment of mixed-lineage leukemia using compounds that induce proteolysis of MLL fusion proteins associated with mixed-lineage leukemia.

Definitions

A hydrocarbyl group is a group comprising only carbon atoms and hydrogen atoms. Thus, hydrocarbyl groups are those derived by the removal of a hydrogen atom from a hydrocarbon compound. Examples of hydrocarbyl groups include alkyl groups, cycloalkyl groups, aryl groups and aryl groups substituted with one or more alkyl substituents.

An alkyl group is a linear or branched chain saturated hydrocarbyl group. An alkyl group may, for example, be a $C_1$-$C_{12}$ alkyl group, a $C_1$-$C_6$ alkyl group, or a $C_1$-$C_3$ alkyl group. Examples of a $C_1$-$C_6$ alkyl group are methyl, ethyl, n-propyl, iso-propyl, n-butyl, iso-butyl, sec-butyl, tert-butyl, pentyl, neopentyl and hexyl.

An alkenyl group refers to a group containing one or more carbon-carbon double bonds, which may be branched or unbranched. An alkenyl group may, for example, be a $C_2$-$C_{12}$ alkenyl group, a $C_2$-$C_6$ alkenyl group, or a $C_2$-$C_4$ alkenyl group.

An alkynyl group refers to a group containing one or more carbon-carbon triple bonds, which may be branched or unbranched. An alkynyl group may, for example, be a $C_2$-$C_{12}$ alkynyl group, a $C_2$-$C_6$ alkynyl group, or a $C_2$-$C_4$ alkynyl group.

An alkyl group, alkenyl group or alkynyl group is unsubstituted or substituted. Typically, an alkyl group is unsubstituted or substituted with up to three substituents, preferably unsubstituted or substituted with up to two substituents, more preferably unsubstituted or substituted with one substituent and most preferably unsubstituted.

A cycloalkyl group is a monocyclic or polycyclic saturated hydrocarbon group. A cycloalkyl group may, for example, be a $C_5$-$C_{12}$ cycloalkyl group, a $C_6$-$C_{12}$ cycloalkyl group or a $C_6$-$C_{10}$ cycloalkyl group. Monocylic cycloalkyl groups include cyclopentyl, cyclohexyl, cycloheptyl, cyclooctyl, cyclononyl, cyclodecyl, cycloundecyl and cyclododecyl. Polycyclic cycloalkyl groups may be fused or spiro cycloalkyl groups. Examples of polycyclic cycloalkyl include adamantyl (including both 1-adamantyl and 2-adamantyl), norbornyl (including 1-norbornyl, 2-norbornyl and 7-norbornyl) and decalinyl (including 1-decalinyl, 2-decalinyl and 3-decalinyl).

A cycloalkyl group is unsubstituted or substituted. Typically, a cycloalkyl group is unsubstituted or substituted with up to three substituents, preferably unsubstituted or substituted with up to two substituents and more preferably unsubstituted or substituted with one substituent.

An aryl group is a monocyclic, bicyclic or polycyclic aromatic ring which contains from 6 to 16 carbon atoms, often from 6 to 10 carbon atoms, in the ring portion. Examples include phenyl, naphthyl, indenyl, indanyl, anthracenyl and pyrenyl groups. Often an aryl group is phenyl.

Typically, an aryl group is unsubstituted or substituted with up to three substituents, preferably unsubstituted or substituted with up to two substituents and more preferably unsubstituted or substituted with one substituent.

A heteroaryl group is a monocyclic or bicyclic heteroaromatic ring which typically contains from five to ten atoms in the ring portion including one or more heteroatoms (such a group being identified herein as a 5 to 10-membered ring heteroaryl group). A heteroaryl group contains at least one heteroatom selected from O, S and N. It may contain, for example, one, two, three or four, e.g. one or two, heteroatoms. Examples of heteroaryl groups include pyridyl, pyrazinyl, pyrimidinyl, pyridazinyl, furanyl, thienyl, pyrazolidinyl, pyrrolyl, tetrazolyl, oxazolyl, oxadiazolyl, isoxazolyl, thiadiazolyl, thiazolyl, isothiazolyl, imidazolyl, pyrazolyl, quinolyl and isoquinolyl. Examples of preferred heteroaryl groups are pyridyl, pyrrolyl, tetrazolyl or oxazolyl.

Typically, a heteroaryl group is unsubstituted or substituted with up to three substituents, preferably unsubstituted or substituted with up to two substituents and more preferably unsubstituted or substituted with one substituent.

As used herein, a 5- to 10-membered heterocyclyl group is a non-aromatic, saturated or unsaturated, monocyclic or polycyclic $C_{5-10}$ carbocyclic ring system in which one or more, for example 1, 2, 3 or 4, of the carbon atoms are replaced with a moiety selected from N, O, S, S(O) and $S(O)_2$. Preferably, the 5- to 10-membered heterocyclyl group is a 5- to 6-membered ring.

Examples of heterocyclyl groups include azetidinyl, oxetanyl, thietanyl, pyrrolidinyl, imidazolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, methylenedioxyphenyl, ethylenedioxyphenyl, thiomorpholinyl, S-oxo-thiomorpholinyl, S,S-dioxo-thiomorpholinyl, morpholinyl, 1,3-dioxolanyl, 1,4-dioxolanyl, trioxolanyl, trithianyl, imidazolinyl, pyranyl, pyrazolinyl, thioxolanyl, thioxothiazolidinyl, 1H-pyrazol-5-(4H)-onyl, 1,3,4-thiadiazol-2(3H)-thionyl, oxopyrrolidinyl, oxothiazolidinyl, oxopyrazolidinyl, succinimido and maleimido groups and moieties. Preferred heterocyclyl groups are pyrrolidinyl, imidazolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, thiomorpholinyl and morpholinyl groups and moieties. More preferred heterocyclyl groups are tetrahydropyranyl, tetrahydrothiopyranyl, thiomorpholinyl, tetrahydrofuranyl, tetrahydrothienyl, piperidinyl, morpholinyl and pyrrolidinyl groups.

Examples of substituents for alkyl, alkenyl and alkynyl groups include —OH, —SH and halogen. Preferred such substituents are —OH and halogen, especially halogen. If an alkyl, alkenyl or alkynyl group has two or more substituents, then each substituent can be the same or different.

Examples of substituents for cycloalkyl groups, aryl groups, heteroaryl and heterocyclyl groups include $C_1$-$C_6$ alkyl, —$OR^{S1}$, —$SR^{S1}$, halogen, —$NO_2$, —CN, —COOH, —$NR^{S1}R^{S2}$, —$C(O)NR^{S1}R^{S2}$ and —$N(R^{S1})C(O)R^{S2}$ substituents, in which $R^{S1}$ and $R^{S2}$ are, independently of one another, hydrogen or a $C_1$-$C_6$ alkyl group.

It will be appreciated that —$OR^{S1}$ includes a hydroxyl substituent (when $R^{S1}$ is hydrogen) and an alkoxy substituent (when $R^{S1}$ is $C_1$-$C_6$ alkyl). Similarly, —$SR^{S1}$ includes a thiol substituent —SH (when $R^{S1}$ is hydrogen) and an alkylthiol substituent (when $R^{S1}$ is $C_1$-$C_6$ alkyl). The substituent —$NR^1R^{S2}$ can be a primary amine (when $R^{S1}$ and $R^{S2}$ are both hydrogen), a secondary amine (when one of $R^{S1}$ and $R^{S2}$ is hydrogen and the other is $C_1$-$C_6$ alkyl) or a tertiary amine (when both of $R^{S1}$ and $R^{S2}$ are $C_1$-$C_6$ alkyl). If a cycloalkyl group, aryl group, heteroaryl or heterocyclyl group has two or more substituents, then each substituent can be the same or different.

Preferred substituents for cycloalkyl groups, aryl groups, heteroaryl groups and heterocyclyl groups include $C_1$-$C_6$ alkyl, —$OR^{S1}$, halogen and —$NR^{S1}R^{S2}$ substituents, in which $R^{S1}$ and $R^{S2}$ are, independently of one another, hydrogen or a $C_1$-$C_6$ alkyl group. Particularly preferred substituents include $C_1$-$C_6$ alkyl and halogen.

A halogen group is a chlorine, fluorine, bromine or iodine group (a chloro group, a fluoro group, a bromo group or an iodo group). A halogen group is often a chlorine or fluorine group, for example a chlorine group.

Unless the context clearly dictates otherwise, the terms "substituent" and "group" are herein used interchangeably. Thus, the definitions provided herein in relation to a particular "group" (e.g., an alkyl group) apply interchangeably to the corresponding "substituent" (e.g., an alkyl substituent).

Compound Capable of Promoting the Proteolyis of MLL Fusion Proteins Associated with Mixed Lineage Leukemia Compounds suitable for use in accordance with the present invention are those that are capable of promoting the proteolyis of MLL fusion proteins associated with mixed lineage leukemia. Specifically, the MLL fusion proteins at issue are those resulting from the chromosomal translocations affecting the MLL gene at 11q23 in mixed lineage leukemia.

The ability of a compound to promote proteolysis of the MLL fusion proteins can be determined by comparing the degree of proteolysis of a sample of MLL fusion proteins both in the presence and in the absence of the test compound. An increased degree of proteolysis in the presence of the test compound, compared with in its absence, indicates that the compound is capable of promoting the proteolyis of MLL fusion proteins associated with mixed lineage leukemia. Those skilled in the art are familiar with the design and implementation of assay methods to test compounds for their ability to degrade a given protein. Merely by way of example, one suitable method for selecting a suitable compound for use in accordance with the present invention involves carrying out an assay such as that described in Example 4.

An exemplary compound is a thiuram disulfide or a dithiocarbamic acid, or a pharmaceutically acceptable salt or ester thereof. For example, the compound may be a compound of the formula (1) or (2)

or a pharmaceutically acceptable salt or ester thereof; wherein:

$R_1$, $R_2$, $R_3$ and $R_4$ are the same or different and are independently selected from hydrogen, a $C_1$-$C_{12}$ alkyl group, a $C_2$-$C_{12}$ alkenyl group, a $C_2$-$C_{12}$ alkynyl group, a $C_5$-$C_{12}$ cycloalkyl group, a $C_6$-$C_{16}$ aryl group, a 5 to 10-membered ring heteroaryl group and a 5 to 10-membered ring heterocyclyl group, and wherein one or both of (i) $R_1$ and $R_2$, together with the nitrogen atom to which they are mutually attached, and (ii) $R_3$ and $R_4$, together with the nitrogen atom to which they are mutually attached, can form a 5 to 10-membered ring heteroaryl group or a 5 to 10-membered ring heterocyclyl group; and wherein any cycloalkyl group, aryl group, heteroaryl group or heterocyclyl group is unsubstituted or substituted with up to three substituents S and any alkyl group is either unsubstituted or substituted with up to three substituents S';

each substituent S is independently selected from a $C_1$-$C_6$ alkyl, —$OR^{S1}$, $SR^{S1}$, halogen, —$NO_2$, —CN, —COOH, —$NR^{S1}R^{S2}$, —$C(O)NR^{S1}R^{S2}$ and —$N(R^{S1})C(O)R^{S2}$ substituent, in which $R^{S1}$ and $R^{S2}$ are, independently of one another, hydrogen or a $C_1$-$C_6$ alkyl group; and each substituent S' is independently selected from —OH, —SH and halogen.

Preferably $R_1$, $R_2$, $R_3$ and $R_4$ are the same or different and are independently selected from hydrogen, a $C_1$-$C_6$ alkyl group, a $C_2$-$C_6$ alkenyl group, a $C_2$-$C_6$ alkynyl group, a $C_5$-$C_6$ cycloalkyl group, a $C_6$-$C_{10}$ aryl group, a 5 to 10-membered ring heteroaryl group and a 5 to 10-membered ring heterocyclyl group; and wherein any cycloalkyl group, aryl group, heteroaryl group or heterocyclyl group is unsubstituted or substituted with up to two S and any alkyl group is either unsubstituted or substituted with up to two S'. Still more preferably $R_1$, $R_2$, $R_3$ and $R_4$ are the same or different and are independently selected from hydrogen and a $C_1$-$C_6$ alkyl group, most preferably a $C_1$-$C_6$ alkyl group.

Exemplary compounds include disulfiram and diethyldithiocarbamic acid or a pharmaceutically acceptable salt thereof. It will be appreciated that disulfiram is a compound of the formula (1) in which each of $R_1$, $R_2$, $R_3$ and $R_4$ is ethyl. Diethyldithiocarbamic acid is a compound of the formula (2) in which each of $R_1$ and $R_2$ is ethyl. Diethyldithiocarbamic acid is a metabolite of disulfiram (formed by breakage of the disulfide bond in disulfiram). Disulfiram is a particularly preferred compound for use in the present invention.

Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds for use in this invention include those formed with a pharmaceutically acceptable base (e.g. whereby a salt is formed via abstraction by the base of the hydrogen atom of the —SH moiety in a compound of formula (2)). Suitable such pharmaceutically acceptable salts include alkali metal salts, e.g. sodium or potassium salts; alkaline earth metal salts, e.g. calcium or magnesium salts; ammonium salts; and salts formed with suitable organic ligands, e.g. quaternary ammonium salts, and meglumine salts.

Standard principles similarly underlie the selection and preparation of pharmaceutically acceptable esters. A pharmaceutically acceptable ester is typically an ester that is capable of hydrolysis under physiological conditions to produce its corresponding acid. Examples of suitable esters include $C_{1-6}$ alkynyl, alkenyl and alkyl esters or such esters in which one of the carbon atoms of the $C_{1-6}$ alkynyl, alkenyl or alkyl group (along with any hydrogen atoms to which it is attached) is replaced by phenyl. Specific examples include $C_{1-6}$ alkyl and phenyl esters, e.g. $C_{1-4}$ alkyl esters (such as methyl, ethyl, propyl, isopropyl, butyl, isobutyl or tert-butyl ester) and phenyl esters.

Any pharmaceutically acceptable salt or ester of a compound of formula (1) or (2) is for example a pharmaceutically acceptable salt or ester of a compound of formula (2). It will be readily appreciated that the dithiocarbamic acid moiety in formula (2) is susceptible to salt formation (via loss of the proton on the —SH group) or esterification (via reaction at the —SH group).

Figure 1:
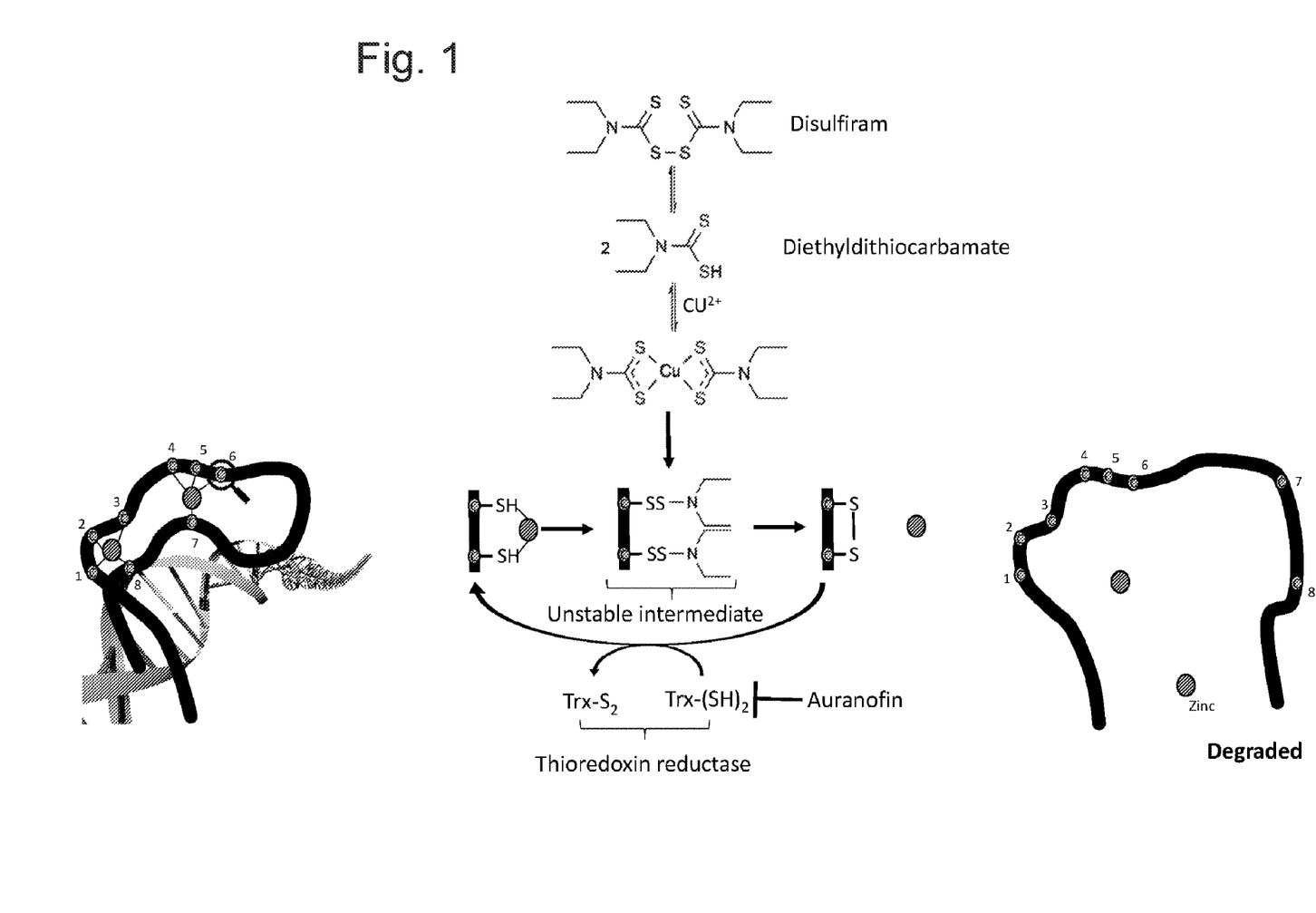
FIG. 1 provides a schematic representation of a possible mechanism of action for compounds outlined in the present disclosure.
Figure 2A:
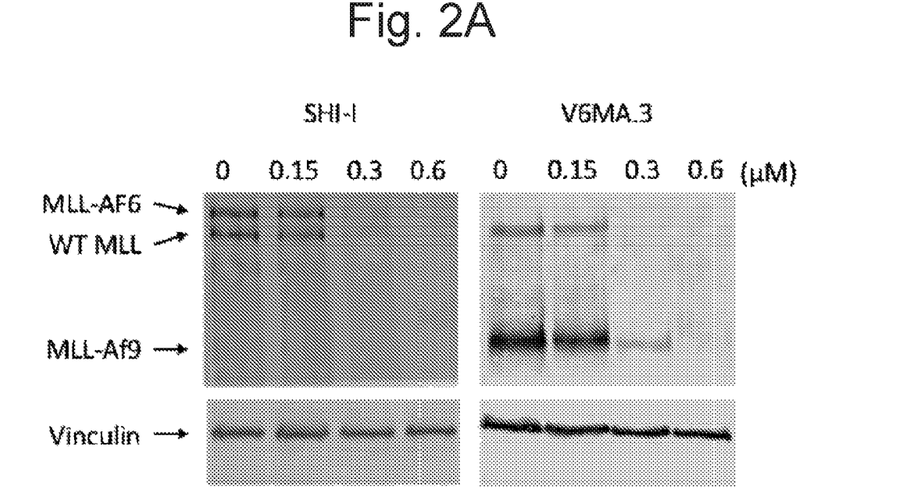
in FIG. 2A, Western blot analysis after 16 hrs of disulfiram treatment in the presence of copper of MLL-AF6 positive cell line SHI-I and MLL-AF9 immortalised cord blood V6MA.3, showing proteolysis of the MLL-fusion protein; and, in FIG. 2B, the effect of copper on the effectiveness of disulfiram ("DSF") to induce the proteolysis of MLL fusion proteins (also showing proteolysis of the MLL-fusion protein in a primary patient sample).
Figure 2B:
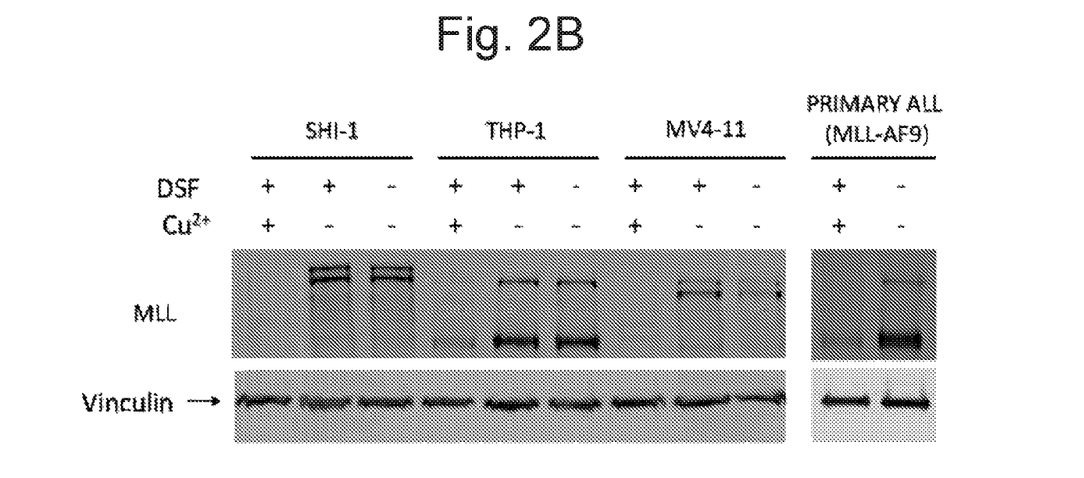
Figure 3:
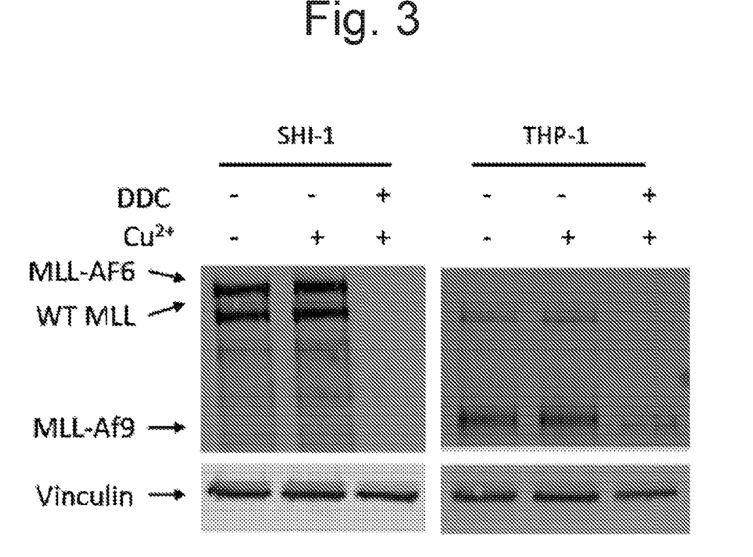
Figure 4A:
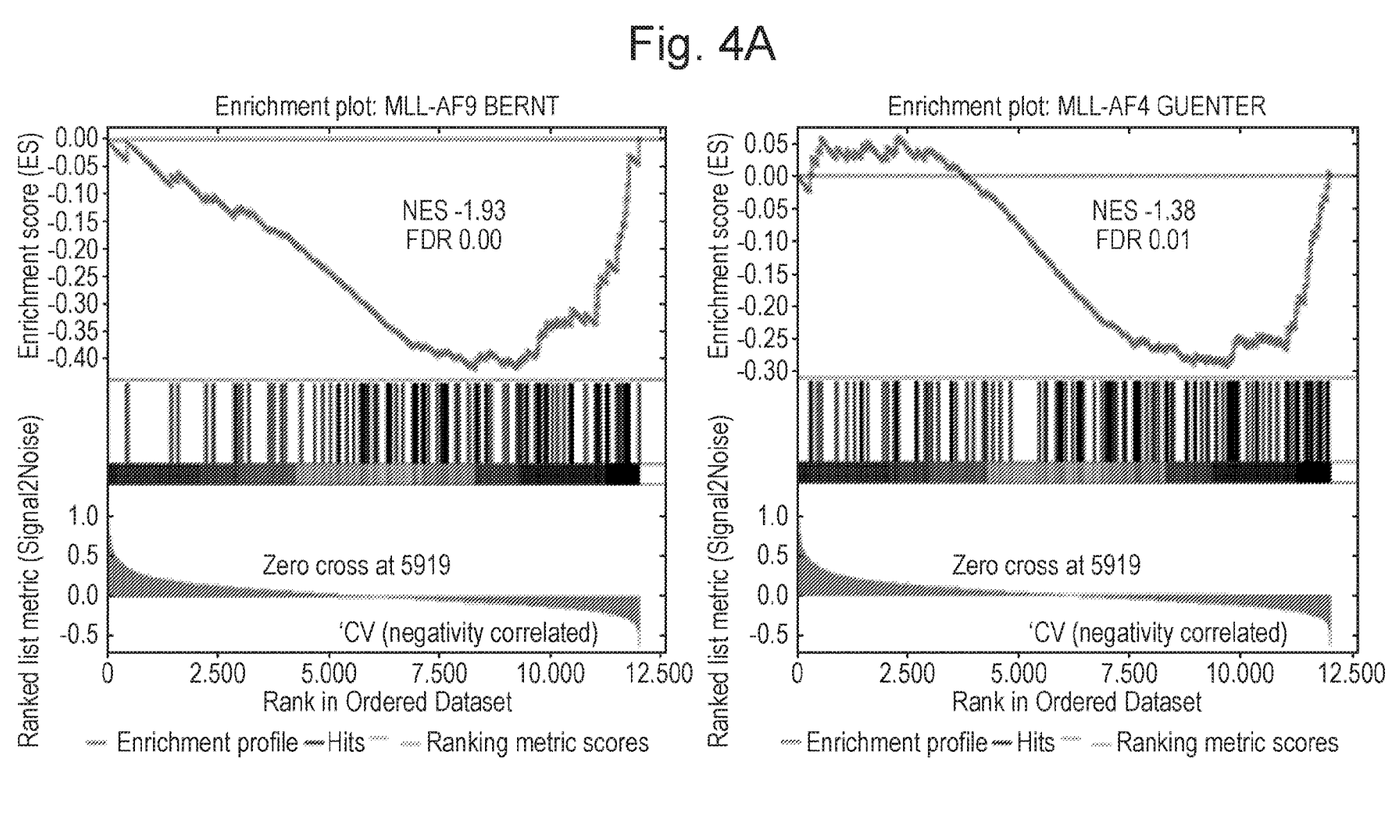
in FIG. 4A, Gene Set Enrichment Analysis of SHI-I cells treated with disulfiram for 16 hrs in the presence of copper, wherein the analysis shows negative enrichment to both published MLL-AF9 and MLL-AF4 profiles; and, in FIG. 4B, RT-qPCR analysis of MLL target gene expression level of HOXA9/HOXA10 and MEIS1, normalised to 18S, after 16 hrs of treatment with disulfiram (concentrations indicated) in SHI-I cells, demonstrating efficient down-regulation of the target genes.
Figure 4B:
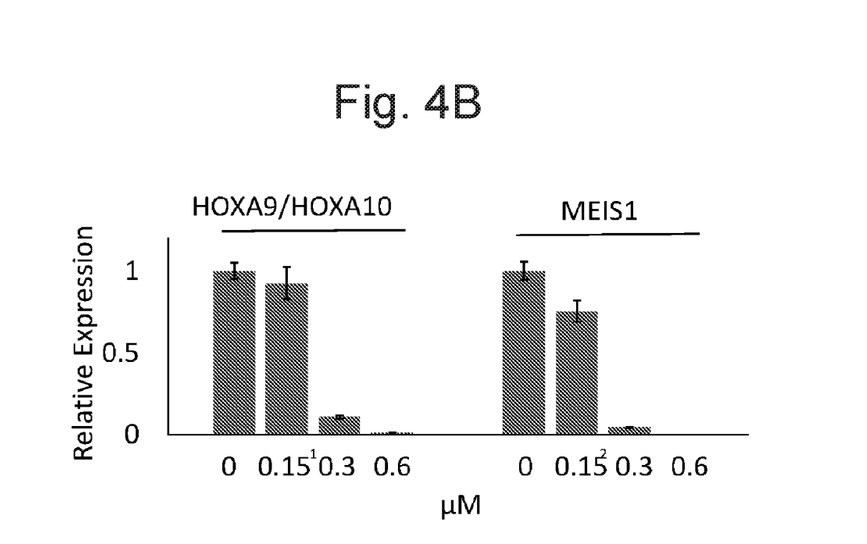
Figure 5:
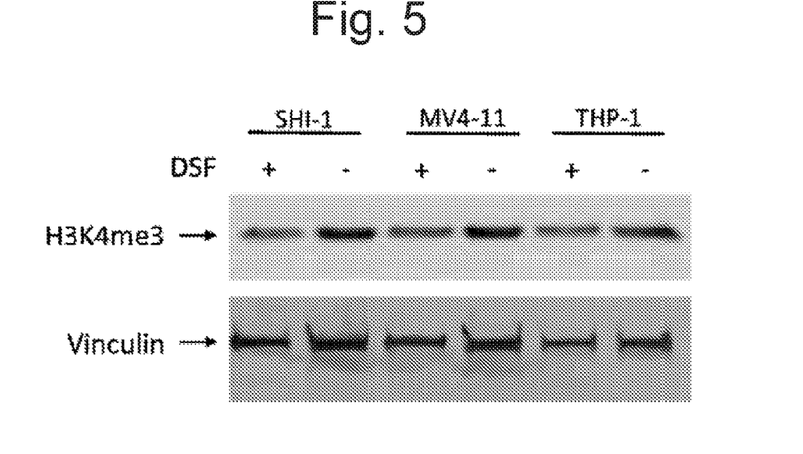
FIG. 5 shows, as explained in Example 1, Western blot analysis after 16 hrs of disulfiram treatment in the presence of copper of various MLL rearranged cell lines, showing a decrease in H3K4me3.

Without being limited by theory, a possible mechanism of action for thiuram disulfide and dithiocarbamic acid compounds (exemplified by disulfiram and diethyldithiocarbamic acid) is schematically illustrated in FIG. 1. The CXXC domain of the MLL fusion protein contains ZnFingers, which stabilise its structure and make it resistant to proteolysis. Dithiocarbamic acid administered either as such or formed in situ as a metabolite of thiuram disulfide is posited to make the ZnFinger more susceptible to thiol-disulfide exchange, destabilising the protein and targeting it for the proteasome. This proposed mechanism is supported by the empirical finding, described in more detail elsewhere herein, that proteolysis is further enhanced by the presence of a thioredoxin reductase inhibitor (thereby inhibiting the reconversion of protein disulfides to ZnFingers). It will be readily apparent that such a mechanism of action, involving the degradation of the MLL fusion proteins driving this cancer phenotype, differs from any mechanism of action by which disulfiram or related compounds might hypothetically function in relation to treatment of cancers not associated with MLL fusion proteins (e.g. leukemias not characterized by the presence of MLL fusion proteins). Indeed, the distinctive mechanism of action described above may be associated with the strikingly high specificity and effectiveness of the compounds in treating MLL.

Therapy, Pharmaceutical Compositions and Route of Administration

The compounds of the invention are for use in the treatment of mixed lineage leukemia, typically in a human patient. Most commonly the treatment comprises treatment of a pediatric patient, i.e. a patient under 18 years of age. For example, the pediatric patient may be an infant patient of 1 year or less in age, such as an infant patient in the first 6 months of life. However, it is to be emphasized that the techniques of the present invention can be applied to any patient suffering mixed lineage leukemia, including adult (18 years or older) patients.

As explained elsewhere herein, mixed lineage leukemia refers to leukemia that is characterized by the presence of MLL fusion proteins that are the result of chromosomal translocations affecting the MLL gene at 11q23. The leukemia can, for example, be an acute lymphoblastic leukemia (ALL) or an acute lymphoblastic myeloid leukemia (AML). Thus, the principles of the present invention provide for efficacious treatment of patients exhibiting MLL fusion proteins resulting from chromosomal translocations affecting the MLL gene at 11q23, inclusive of those further characterized as suffering from either of AML and ALL.

The compounds of the invention may be administered as pharmaceutical compositions in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

The one or more pharmaceutically acceptable excipients or diluents may be any suitable excipients or diluents. For example, a pharmaceutical composition which is a solid oral form may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tableting, sugar coating, or film coating processes.

A pharmaceutical composition which is a liquid dispersion for oral administration may be a syrup, emulsion and suspension. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

Pharmaceutical compositions of the invention may comprise additional active ingredients, such as an additional therapeutic agent intended, for example, for the treatment of the same condition or a different one, or for other purposes such as amelioration of side effects. Non-limiting examples include other anti-cancer drugs, heavy metal ions such as those described in US 2004/019102 (e.g. ions of arsenic, bismuth, cobalt, copper, chromium, gallium, gold, iron, manganese, nickel, silver, titanium, vanadium, selenium or zinc) and tyrosine kinase inhibitors such as those described in WO 2014/128235 (the contents of both of these patent applications are herein incorporated by reference in their entirety). As further described elsewhere herein the pharmaceutical compositions of the invention may also comprise a thioredoxin reductase inhibitor.

More generally, the subject-matter of the invention extends to combination therapies in which additional active ingredients such as those outlined herein are administered. For example, all references herein to a thioredoxin reductase inhibitor in pharmaceutical compositions, products, compounds for use, uses and methods of treatment of the present invention can be substituted for references to an "additional active ingredient", such as those outlined herein.

Dosages and Dosage Regimes

A suitable dosage of the compound capable of promoting the proteolyis of MLL fusion proteins associated with mixed lineage leukemia may be determined by a skilled medical practitioner. Typically the dosage of the compound is 1 to 1000 mg per day, preferably 50 to 600 mg per day, for example about 100 to about 400 mg per day, such as about 250 mg per day. Dosages of any other active agents used, for example a thioredoxin reductase inhibitor, may also be determined by a skilled medical practitioner but typically may be 1 to 500 mg per day, preferably 10 to 250 mg per day, for example about 25 or about 50 mg per day.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. Thus, the dosage is typically an effective or therapeutically effective dosage.

The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Dosage regimens may be adjusted to provide the optimum desired response. For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the drugs in the patient and the duration of treatment desired.

Combination with Thioredoxin Reductase Inhibitor

It has been found that the efficacy of the compound capable of promoting the proteolyis of MLL fusion proteins associated with mixed lineage leukemia is significantly enhanced by the presence of a thioredoxin reductase inhibitor. The enhanced efficacy is typically of a synergistic nature, for example in that it is greater than any merely additive effect that could be extrapolated from the activities of the respective compounds alone. For example, a thioredoxin reductase inhibitor alone may have substantially no efficacy in treating mixed lineage leukemia.

One possible mechanism underlying the enhanced efficacy of the combination is discussed elsewhere herein, namely the inhibition by the thioredoxin reductase inhibitor of reconversion of MLL fusion protein disulfide bonds, produced by disulfiram or similar compounds, back to ZnFingers.

Suitable thioredoxin reductase inhibitors can readily be selected by those skilled in the art. One exemplary such compound is Auranofin, which is a well known anti-rheumatic drug. Another exemplary such compound is Curcumin.

In one aspect, the present invention thus provides a pharmaceutical composition comprising both a compound capable of promoting the proteolyis of MLL fusion proteins associated with mixed lineage leukemia and a thioredoxin reductase inhibitor Such pharmaceutical compositions will typically further comprise one or more pharmaceutically acceptable excipients or carriers.

The present invention also extends to situations where the active ingredients are co-administered. When the active ingredients are co-administered they can be present in separate pharmaceutical compositions. Alternatively, the active ingredients are formulated into a single pharmaceutical composition.

For the avoidance of doubt, in the product comprising (a) a compound that is capable of promoting the proteolyis of MLL fusion proteins associated with mixed lineage leukemia, and (b) a thioredoxin reductase inhibitor, as a combined preparation, the product may comprise either a single pharmaceutical composition that comprises both (a) and (b) or alternatively a first pharmaceutical composition that comprises (a) and a second (i.e., separate) pharmaceutical composition that comprises (b).

Co-administration of the active ingredients according to the present invention includes simultaneous, separate and sequential administration. Typically, both drugs are administered simultaneously or one drug is administered first and the second drug is administered within 12 hours, preferably within 6 hours, more preferably within 3 hours, most preferably within 1 hour after the administration of the first drug.

Co-Administration with Copper

It has also been found that the efficacy of the compound capable of promoting the proteolyis of MLL fusion proteins associated with mixed lineage leukemia is significantly enhanced by the presence of copper, particularly when the the compound is a thiuram disulfide or a dithiocarbamic acid, or a pharmaceutically acceptable salt or ester thereof.

The copper to be co-administered with the compound capable of promoting the proteolyis of MLL fusion proteins associated with mixed lineage leukemia preferably comprises copper (II) ions. Copper (II) ions can readily be provided in any suitable form, for example as a copper (II) salt. One suitable such copper (II) salt is copper chloride ($CuCl_2$). Other copper salts can, however, of course be used. For the avoidance of doubt, when the pharmaceutical composition of the present invention comprises copper then preferred forms of copper are also as discussed in the foregoing passage.

When a treatment involves co-administration with copper, the co-administration includes simultaneous, separate and sequential administration (with the compound capable of promoting the proteolyis of MLL fusion proteins associated with mixed lineage leukemia). Typically, the copper is administered simultaneously with the compound capable of promoting the proteolyis of MLL fusion proteins associated with mixed lineage leukemia, but alternatively one of the copper and the compound may be administered first and the other administered within 12 hours, preferably within 6 hours, more preferably within 3 hours, most preferably within 1 hour thereafter.

The present invention is explained in more detail in the following by referring to Examples, which are not to be construed as limitative.

EXAMPLES

Example 1 Disulfiram Induces MLL Degradation and Blocks MLL-Specific Leukemogenesis Cell Culture Human leukaemic cell lines (DSMZ) were cultured in Roswell Park Memorial Institute (RPMI) medium (Invitrogen), supplemented with 10% heat-inactivated FCS, 100 U/ml Penicillin (Invitrogen), 100 µg/ml Streptomycin (Invitrogen) and 2 mM L-glutamine (Invitrogen) (complete RPMI), or in Iscove's Modified Dulbecco's Medium (IMDM) (Invitrogen) supplemented with 20% heat-inactivated FCS, 100 U/ml Penicillin (Invitrogen), 100 µg/ml Streptomycin (Invitrogen) and 2 mM L-glutamine (Invitrogen)(complete IMDM).

SHI-I (MLL-AF6), THP-I (MLL-AF9) and MV4-11 (MLL-AF4) cell lines were treated with 300 nM of Disulfiram (Aldrich) or concentrations indicated and 1 µM of Copper chloride (Acros Organics) unless indicated otherwise for 16 hours.

Preparation of Total Protein Lysates

Cells were lysed in Sample Reducing Buffer (200 mM DTT, 2% sodium dodecyl sulphate (SDS), 10% v/v Glycerol, 0.02% v/v Bromophenol Blue, 125 mM Tris HCl pH 6.8). The lysates were incubated for 5 minutes at 100° C., vortexed for 10 seconds and centrifuged at 13,200 rpm for 10 minutes at 4° C. The total cell lysate was then collected and stored at −20° C. or loaded immediately onto a polyacrylamide gel.

Western Blot

The whole cell lysate was electrophoresed in 7% Bis-Tris polyacrylamide gel and transferred to a odyssey nitrocellulose membrane (LI-COR).

After blocked for 1 hr for non-specific binding in PBS-T with 5% of non-fat milk, blots were incubated with primary antibodies (MLL, mouse monoclonal 1:2000, Millipore; Vinculin, rabbit monoclonal 1:10000, Abcam) overnight at 4° C., followed by secondary IRDye conjugated antibodies (mouse IEDye800CW 1:10000; rabbit IRDye680RD 1:10000, LI-COR) at room temperature.

Blots were visualized using the Odyssey CLx.

Figure 6A:
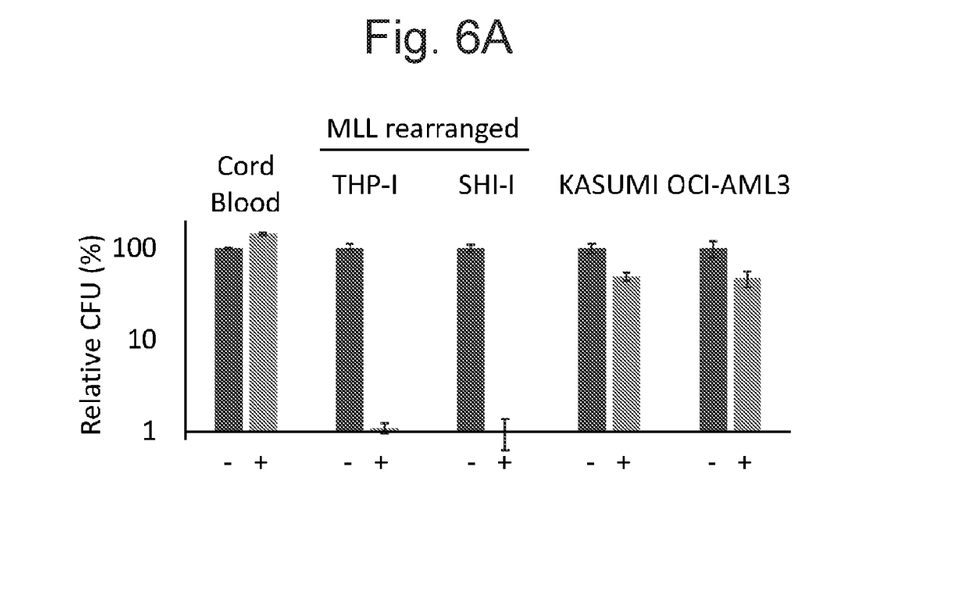
in FIG. 6A, relative CFU corresponding to colony formation in MLL rearranged cells, other leukemic cell lines and CD34+ cord blood, in a methylcellulose colony formation assay after treatment of the cells with 300 nM disulfiram (equal numbers of cells were plated and normalised CFU frequency is shown, with error bars representing standard deviation); and, in FIG. 6B, the corresponding treated and control plates themselves.
Figure 6B:
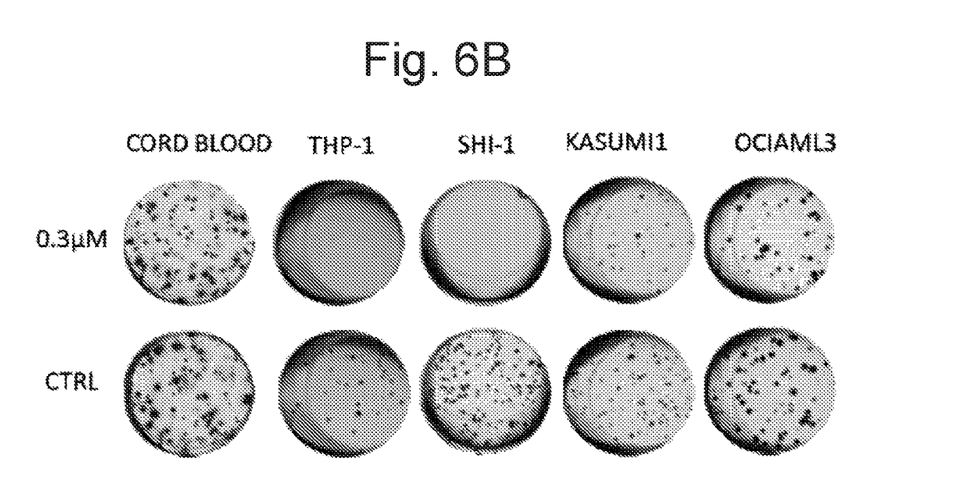
Figure 7:
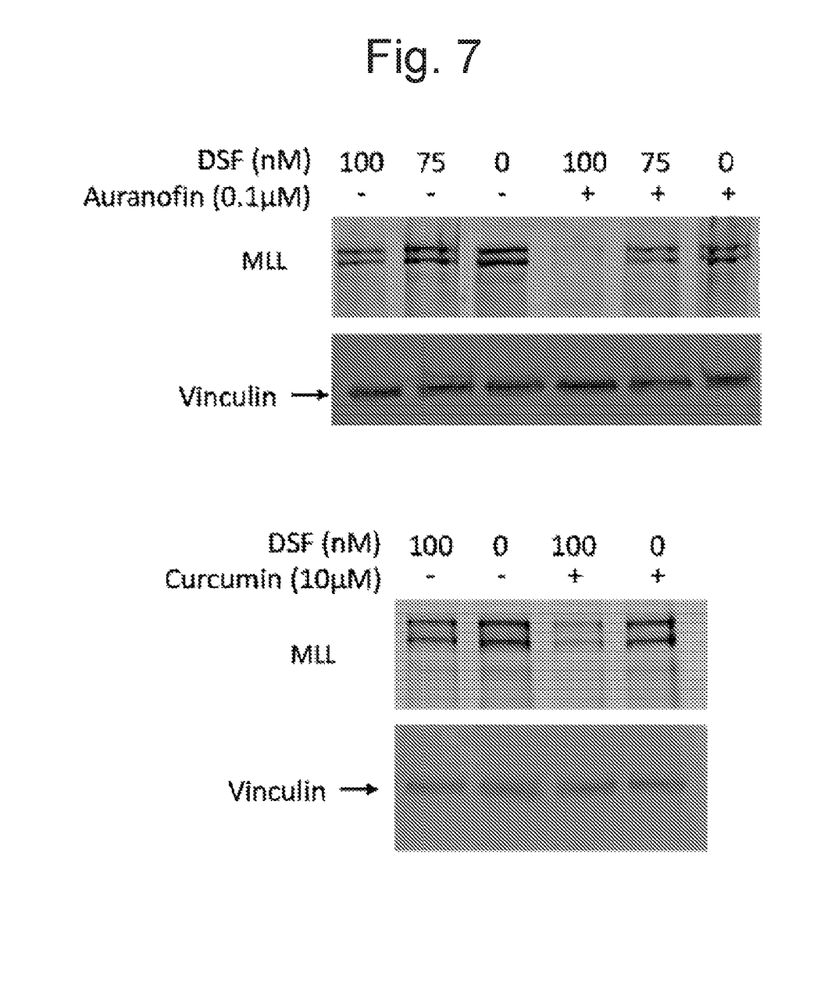
FIG. 7 shows, as explained in Example 3, Western blot analysis after 16 hrs of disulfiram treatment in the presence of Copper of MLL-AF6 positive cell line SHI-I with or without thioredoxin reductase inhibitors Auranofin and Curcumin, showing proteolysis of the MLL-fusion protein.

As shown in FIG. 6, panel A, relative CFU corresponding to colony formation in MLL rearranged cells showed a substantially higher effect than in other (non-MLL) leukemic cell lines and CD34+ cord blood, in the methylcellulose colony formation assay after treatment of the cells with disulfiram.

Example 2 Diethyldithiocarbamate also Induces MLL Degradation and Blocks MLL-Specific Leukemogenesis Cell Culture Human leukaemic cell lines (DSMZ) were cultured in Roswell Park Memorial Institute (RPMI) medium (Invitrogen), supplemented with 10% heat-inactivated FCS, 100 U/ml Penicillin (Invitrogen), 100 µg/ml Streptomycin (Invitrogen) and 2 mM L-glutamine (Invitrogen) (complete RPMI), or in Iscove's Modified Dulbecco's Medium (IMDM) (Invitrogen) supplemented with 20% heat-inactivated FCS, 100 U/ml Penicillin (Invitrogen), 100 µg/ml Streptomycin (Invitrogen) and 2 mM L-glutamine (Invitrogen)(complete IMDM).

SHI-I (MLL-AF6), and THP-I (MLL-AF9) cell lines were treated with 300 nM of Diethyldithiocarbamate (Aldrich) and 1 µM of Copper chloride (Acros Organics) unless indicated otherwise for 16 hours.

Preparation of Total Protein Lysates

Cells were lysed in Sample Reducing Buffer (200 mM DTT, 2% sodium dodecyl sulphate (SDS), 10% v/v Glycerol, 0.02% v/v Bromophenol Blue, 125 mM Tris HCl pH 6.8). The lysates were incubated for 5 minutes at 100° C., vortexed for 10 seconds and centrifuged at 13,200 rpm for 10 minutes at 4° C. The total cell lysate was then collected and stored at −20° C. or loaded immediately onto a polyacrylamide gel.

Western Blot

The whole cell lysate was electrophoresed in 7% Bis-Tris polyacrylamide gel and transferred to a odyssey nitrocellulose membrane (LI-COR).

After blocked for 1 hr for non-specific binding in PBS-T with 5% of non-fat milk, blots were incubated with primary antibodies (MLL, mouse monoclonal 1:2000, Millipore; Vinculin, rabbit monoclonal 1:10000, Abcam) overnight at 4° C., followed by secondary IRDye conjugated antibodies (mouse IEDye800CW 1:10000; rabbit IRDye680RD 1:10000, LI-COR) at room temperature.

Blots were visualized using the Odyssey CLx.

Example 3 Combination of Disulfiram with a Thioredoxin Reductase Inhibitor

Cell Culture

Human leukaemic cell lines (DSMZ) were cultured Iscove's Modified Dulbecco's Medium (IMDM) (Invitrogen) supplemented with 20% heat-inactivated FCS, 100 U/ml Penicillin (Invitrogen), 100 µg/ml Streptomycin (Invitrogen) and 2 mM L-glutamine (Invitrogen)(complete IMDM).

SHI-I (MLL-AF6) cell line was treated with 100 nM or 75 nm of Disulfiram (Aldrich) and 100 nM of Auranofin or 10 µM of Curcumin supplemented with 1 µM of Copper chloride (Acros Organics) for 16 hours.

Preparation of Total Protein Lysates

Cells were lysed in Sample Reducing Buffer (200 mM DTT, 2% sodium dodecyl sulphate (SDS), 10% v/v Glycerol, 0.02% v/v Bromophenol Blue, 125 mM Tris HCl pH 6.8). The lysates were incubated for 5 minutes at 100° C., vortexed for 10 seconds and centrifuged at 13,200 rpm for 10 minutes at 4° C. The total cell lysate was then collected and stored at −20° C. or loaded immediately onto a polyacrylamide gel.

Western Blot

The whole cell lysate was electrophoresed in 7% Bis-Tris polyacrylamide gel and transferred to a odyssey nitrocellulose membrane (LI-COR).

After blocked for 1 hr for non-specific binding in PBS-T with 5% of non-fat milk, blots were incubated with primary antibodies (MLL, mouse monoclonal 1:2000, Millipore; Vinculin, rabbit monoclonal 1:10000, Abcam) overnight at 4° C., followed by secondary IRDye conjugated antibodies (mouse IEDye800CW 1:10000; rabbit IRDye680RD 1:10000, LI-COR) at room temperature.

Blots were visualized using the Odyssey CLx.

Example 4 Compound Screening Assay

An indicator leukemic fusion gene cell line was constructed that can be used to identify novel drugs that can inhibit the fusion genes. The cell lines are based on the stable expression of the oncogenic fusion gene fused to a Luciferase reporter, plus a control reporter plasmid. In the screen, compounds that reduce luciferase activity, but have no major effect on the control reporter, would be identified for further analysis as potential inhibitors of leukaemia. The MLL-AF9 was fused to luciferase using a PCR based cloning technique. The MLL-AF9-luciferase (called MAcLuc hereinafter) was cloned into pMSCVneo retroviral expression vector and in transient expression assays. The human leukaemic cell line THP1 was transduced with the MSCVneo-MAcLUC and selected with neomycin. Selected cells were single cell FACS sorted and single cell clones were screened for the desired phenotype: Luciferase activity >100× over background. Subsequently, these clones were transduced with MSCVpuro-Renilla and selected with puromycin. Selected cells were single cell FACS sorted and single cell clones were screened for the desired phenotype: Renilla activity >100× over background.

The MSCVneo-MAcLUC reporter supports the constitutive, intracellular synthesis of a novel fusion protein composed of the MLL-AF9 and firefly luciferase in human AML cell line THP1. All manual screenings were performed using 96-well plates 105 of the reporter cells were incubated overnight at 37° C., 5% $CO_2$. The next day compounds were added at a 10 μM final concentration, plates were incubated for 6 hrs at 37° C., and luciferase and renilla activity was measured using Dual-Luciferase Reporter Assay System (Promega). Each plate had two internal standards, untreated and DMSO treated cells. The reporter inactivation (%) was calculated as a ratio of the decrease of the luciferase/renilla ratio compared to DMSO control. Hits were defined as those with a decrease of greater than 30%.

For the exemplified screen, the Prestwick Chemical Library was used. The library contains 1200 small molecules, 100% FDA approved drugs. Active compounds were selected for their high chemical and pharmacological diversity as well as for their known bioavailability and safety in humans.

Example 5 FACS Analysis of Spleen from Non-Irradiated NOD Scid Gamma Mice Transplanted with $10^6$ MLL/AF9 Leukemia Cells Mice were randomly assigned to treatment groups (4 mice in each group): vehicle control (V=5% DMSO, 5% EtOH, 90% corn oil); or disulfiram ("DSF") (50 mg/kg in V) and Cu (0.5 mg/kg in saline).

Mice were treated for 5 consecutive days. Mice were sacrificed 3 days after finishing the treatment, at which point $10^6$ splenocytes were taken and the leukocyte differentiation status was tested. For detection of the cell differentiation antigen CD11b, $10^6$ splenocytes were washed twice with PBS, incubated with APC-conjugated CD11b antibody at 4° C. for 30 min and analyzed by flow cytometry.

Figure 8:
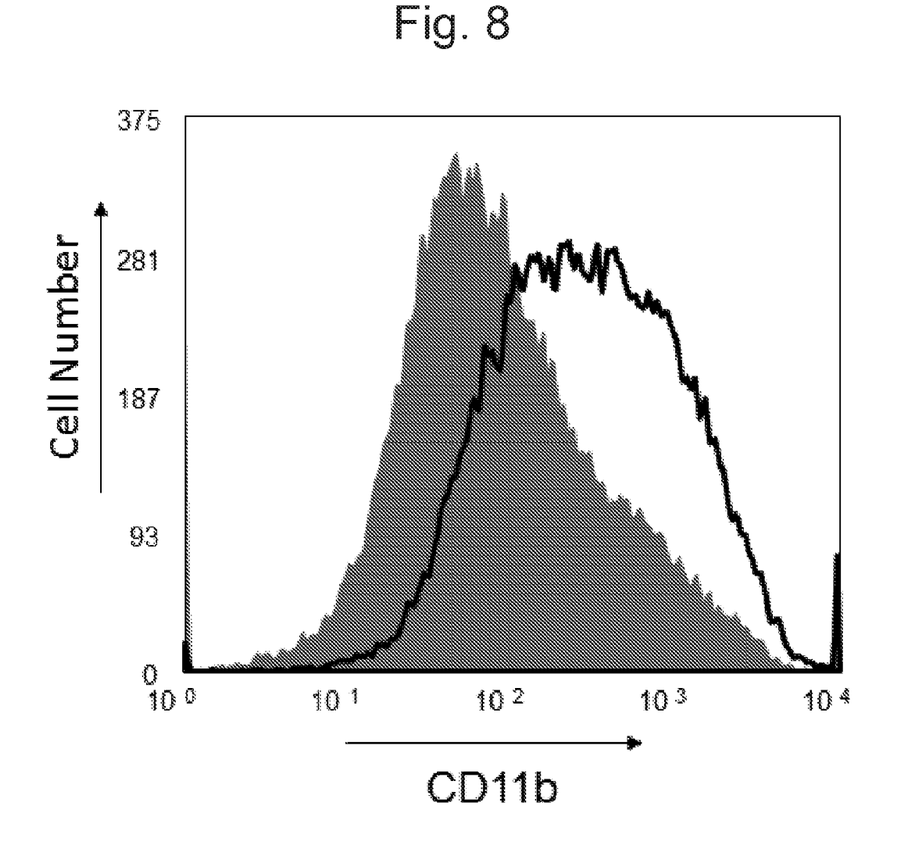
FIG. 8 shows, as explained in Example 5, FACS analysis of spleen from non-irradiated NOD scid gamma mice transplanted with $10^6$ MLL/AF9 leukemia cells. Vehicle control treatment results are shown in solid grey and the disulfiram+Cu treatment results are shown as the black line.

Results are shown in FIG. 8 where the vehicle control results are shown in solid grey and the disulfiram+Cu results are shown as the black line. Treatment with disulfiram+Cu resulted in differentiation of blasts as measured by CD1 lb upregulation.

The invention claimed is:

1. A method for treating mixed lineage leukemia (MLL) in a patient in need thereof, the method comprising: identifying said patient as having MLL; administering to said patient a therapeutically effective amount of a compound that is: (i) disulfiram; or (ii) diethyldithiocarbamic acid; or a pharmaceutically acceptable salt thereof, and inducing proteolysis of MLL fusion proteins associated with mixed lineage leukemia in said patient.

2. The method according to claim 1, which comprises co-administering with copper.

3. The method according to claim 1, which comprises co-administering with a thioredoxin reductase inhibitor.

4. The method according to claim 2, which comprises co-administering with a thioredoxin reductase inhibitor.

5. The method according to claim 3, wherein the thioredoxin reductase inhibitor is Auranofin or Curcumin.

6. The method according to claim 4, wherein the thioredoxin reductase inhibitor is Auranofin or Curcumin.

7. The method according to claim 1, wherein the mixed lineage leukemia is in a patient suffering from acute lymphoblastic leukemia (ALL).

8. The method according to claim 1, wherein the mixed lineage leukemia is in a patient suffering from acute lymphoblastic myeloid leukemia (AML).

9. The method according to claim 1, wherein the compound is disulfiram.

* * * * *